US008669060B2

(12) United States Patent
Markowitz et al.

(10) Patent No.: US 8,669,060 B2
(45) Date of Patent: Mar. 11, 2014

(54) **METHODS AND COMPOSITIONS FOR DETECTING CANCERS ASSOCIATED WITH METHYLATION OF *HMLH1* PROMOTER DNA**

(75) Inventors: Sanford Markowitz, Pepper Pike, OH (US); William Grady, Nashville, TN (US)

(73) Assignee: Case Western Reserve University, Cleveland, OH (US)

( * ) Notice: Subject to any disclaimer, the term of this patent is extended or adjusted under 35 U.S.C. 154(b) by 397 days.

(21) Appl. No.: 11/029,261

(22) Filed: Jan. 5, 2005

(65) Prior Publication Data

US 2005/0153351 A1    Jul. 14, 2005

Related U.S. Application Data (62) Division of application No. 09/957,661, filed on Sep. 20, 2001, now Pat. No. 6,858,388.

(60) Provisional application No. 60/234,087, filed on Sep. 20, 2000.

(51) Int. Cl.
*C12Q 1/68* (2006.01)
*C12P 19/34* (2006.01)
*C07H 21/04* (2006.01)

(52) U.S. Cl.
USPC .................. 435/6.12; 435/91.2; 536/24.3

(58) Field of Classification Search
USPC .................. 435/6, 91.2, 6.12; 536/23.4
See application file for complete search history.

(56) References Cited

U.S. PATENT DOCUMENTS

| | | | | |
|---|---|---|---|---|
| 5,763,227 | A | * | 6/1998 | Blocker ..................... 435/91.1 |
| 6,017,709 | A | * | 1/2000 | Hardin et al. ................ 435/6 |
| 2002/0068293 | A1 | * | 6/2002 | Delenstarr et al. ............. 435/6 |

OTHER PUBLICATIONS

The nucleic acid search report.*
Buck et al. BioTechniques, 1999, vol. 27(3), p. 528-536.*
Lowe et al. Nucleic Acids Research, 1990, vol. 18(7), p. 1757-1762.*
"Identification of Differentially Methylated Sequences in Colorectal Cancer by Methylated CpG Island Amplification" by Toyota, et al., *Cancer Research*, 59, 2307-2312, May 15, 1999.
"CpG island methylator phenotype in colorectal cancer" by Toyota, et al., *Proc. Natl. Acad. Sci. USA*, vol. 96, pp. 8681-8686, Jul. 1999.
"Methylation in hMLH1 promoter interferes with its binding to transcription factor CBF and inhibits gene expression" by Deng, et al., *Oncogene*, (2001) 20, 7120-7127.
"Methylation Pattern of Different Regions of the *MLH1* Promoter and Silencing of Gene Expression in Hereditary and Sporadic Colorectal Cancer" by Menigatti, et al., *Genes, Chromosomes & Cancer*, 31:357-361 (2001).

"Extensive Methylation of h*MLH1* Promoter Region Predominates in Proximal Colon Cancer with Microsatellite Instability" by Miyakura, et al., *Gastroenterology*, 2001; 121:1300-1309.
"Bethesda Guidelines: Relation to Microsatellite Instability and *MLH1* Promoter Methylation in Patients with Colorectal Cancer" by Raedle, et al., *Ann Intern Med.*, 2001; 135:566-576.
"Biallelic inactivation of *hMLH1* by epigenetic gene silencing, a novel mechanism causing human MSI cancers"by Veigl, et al., *Proc. Natl. Acad. Sci. USA*, vol. 95, pp. 8698-8702, Jul. 1998.
"Incidence and functional consequences of *hMLH1* promoter hypermethylation in colorectal carcinoma" by Herman, et al., *Proc. Natl. Acad. Sci. USA*, vol. 95, pp. 6870-6875, Jun. 1998.
"Methylation of the *hMLH1* Promoter Correlates with Lack of Expression of hMLH1 in Sporadic Colon Tumors and Mismatch Repair-defective Human Tumor Cell Lines" by Kane, et al., *Cancer Research*, 57, 808-811, Mar. 1, 1997.
"Hypermethylation of the *hMLH1* Promoter in Colon Cancer with Microsatellite Instability" by Cunningham, et al., *Cancer Research*, 58, 3455-3460, Aug. 1, 1998.
"Methylation of CpG in a Small Region of the hMLH1 Promoter Invariably Correlates with the Absence of Gene Expression" by Deng, et al., *Cancer Research*, 59, 2029-2033, May 1, 1999.
"Age-related Hypermethylation of the 5' Region of *MLH1* in Normal Colonic Mucosa is Associated with Microsatellite-unstable Colorectal Cancer Development" by Nakagawa, et al., *Cancer Research*, 61, 6991-6995, Oct. 1, 2001.
"Molecular Detection of *p16* Promoter. Methylation in the Serum of Patients with Esophageal Squamous Celll Carcinoma" by Hibi, et al., *Clinical Cancer Research*, vol. 7, 3135-3138, Oct. 2001.
"Gene Promoter Hypermethylation in Tumors and Serum of Head and Neck Cancer Patients" by Sanchez-Cespedes, et al., *Cancer Research*, 60, 892-895 Feb. 15, 2000.
"Detection of Aberrant Promoter Hypermethylation of Tumor Suppressor Genes in Serum DNA from Non-Small Cell Lung Cancer Patients" Esteller, et al., *Cancer Research*, 59 67-70, Jan. 1, 1999.
"Hypermethylation APC DNA in Plasma and Prognosis of Patients with Esophageal Adenocarcinoma" by Kawakami, et al. *Journal of the National Cancer Institute*, vol. 92, No. 22, Nov. 15, 2000.
"Aberrant DNA methylation of the p16$^{INK4s}$ gene in plasma DNA of breast cancer patients", by Silva, et al., *British Journal of Cancer* (1999) 80(8), 1262-1264.
"Detection of Aberrant *p16* Methylation in the Plasma and Serum of Liver Cancer Patients" by Wong, et al., *Cancer Research*, 59, 71-73, Jan. 1, 1999.
"Predicting Lung Cancer by Detecting Aberrant Promoter Methylation in Sputum" by Palmisano, et al., *Cancer Research*, 60, 5954-5958, Nov. 1, 2000.
"Fluorescent Methylation-specific Polymerase Chain Reaction for DNA-based Detection of Prostate Cancer in Bodily Fluids" by Goessl, et al., *Cancer Research*, 60, 5941-5945, Nov. 1, 2000.

(Continued)

*Primary Examiner* — Kenneth R. Horlick
*Assistant Examiner* — Joyce Tung
(74) *Attorney, Agent, or Firm* — Ropes & Gray LLP (57) ABSTRACT

Methods are provided for detection of cancers associated with methylation of hMLH1 promoter DNA in a subject. The method comprise assaying for the presence of methylated hMLH1 promoter DNA in a bodily fluid from a subject. In one embodiment, the method comprises reacting DNA from the sample with a chemical compound that converts non-methylated cytosine bases but not methylated cytosine bases, to a different nucleotide base. The compound-converted DNA is then amplified using a methylation-sensitive polymerase chain reaction (MSP) employing primers that amplify the compound-converted DNA template. The present invention also provides nucleotide primer sequences for use in the methylation-sensitive PCR assay.

3 Claims, 6 Drawing Sheets

(56) References Cited

OTHER PUBLICATIONS

"Colorectal Cancer Screening by Detection of Altered Human DNA in Stool: Feasibility of a Multitarget Assay Panel" by Ahlquist, et al., *Gastroenterology*, 2000; 119:1219-1227.

"Detecting Colorectal Cancer in Stool With the Use of Multiple Genetic Targets" by Dong, et al., *Journal of the National Cancer Institute*, vol. 93, No. 11, Jun. 6, 2001.

"Epigenetic phenotypes distinguish microsatellite-stable and -unstable colorectal cancers" by Kuismanen, et al., *PNAS*, Oct. 26, 1999, vol. 96, No. 22, pp. 12661-12666.

"Molecular Screening for Hereditary Nonpolyposis Colorectal Cancer: A Prospective, Population-Based Study" by Percesepe, et al., *Journal of Clinical Oncology*, vol. 19, No. 19, Oct. 1, 2001, pp. 3944-3950.

"Correlation of Methylation of the *hMLH1* Promoter with Lack of Expression of hMLH1 in Sporadic Gastric Carcinomas with Replication Error" by Kang, et al, *Laboratory Investigation*, vol. 79, No. 7, p. 903-909, 1999.

"*hMLH1* Promoter Methylation and Lack of hMLH1 Expression in Sporadic Gastric Carcinomas with High Frequency Microsatellite Instability" by Leung, et al., *Cancer Research*, 59, 159-164, Jan. 1, 1999.

"Frequent Hypermethylation of the *hMLH1* Gene Promoter in Differentiated-Type Tumors of the Stomach with the Gastric Foveolar Phenotype" by Endoh, et al., *American Journal of Pathology*, vol. 157, No. 3, Sep. 2000, pp. 717-722.

"Hypermethylation of the *hMLH1* Gene Promoter in Human Gastric Cancers with Microsatellite Instability" by Fleisher, et al., *Cancer Research*, 59, 1090-1095, Mar. 1, 1999.

"Fields of Aberrant CpG Island Hypermethylation in Barrett's Esophagus and Associated Adenocarcinoma" by Eads, et al, *Cancer Research*, 60, 5021-5026, Sep. 15, 2000.

"Epigenetic Patterns in the Progression of Esophageal Adenocarcinoma" by Eads, et al., *Cancer Research*, 61, 3410-3418, Apr. 15, 2001.

"Hypermethylation of Multiple Genes in Pancreatic Adenocarcinoma" by Ueki, et al., *Cancer Research*, 60, 1835-1839, Apr. 1, 2000.

"CpG Island Methylation in Premalignant Stages of Gastric Carcinoma" by Kang, et al., *Cancer Research*, 61, 2847-2851, Apr. 1, 2001.

"Aberrant Methylation in Gastric Cancer Associated with the CpG Island Methylator Phenotype" . by Toyota, et al., *Cancer Research*, 59, 5438-5442, Nov. 1, 1999.

"Multiple Detection of Genetic Alterations in Tumors and Stool" by Rengucci, et al., *Clinical Cancer Research*, vol. 7, 590-593, Mar. 2001.

"Improved Detection of *K-ras* Codon 12 Mutations in Fecal Exfoliated Cells" by Puig, et al., *Laboratory Investigation*, vol. 79, No. 5, p. 617-618, May 1999.

"A Highly Sensitive Method for K-*ras* Mutation Detection is Useful in Diagnosis of Gastrointestinal Cancer" by Puig, et al., *Int. J. Cancer*, 85, 73-77 (2000).

"Molecular Detection of Genetic Alterations in the Serum of Cotorectal Cancer Patients" by Hibi, et al., *Cancer Research*, 58, 1405-1407, Apr. 1, 1998.

"Detection of mutant K-*ras* DNA in plasma or serum of patients with colorectal cancer" by Kopreski, et al., *British Journal of Cancer*, (1997) 76(10), 1293-1299.

"Detection of Aberrantly Methylated *hMLH1* Promoter DNA in the Serum of Patients with Microsatellite Unstable Colon Cancer" by Grady, et al., *Cancer Research*, 61, 900-902, Feb. 1, 2001.

"Methylation-specific PCR": A novel PCR assay for methylation status of CpG islands by Herman, et al., Proc. Natl. Acad. Sci. USA, vol. 93, pp. 9821-9826, Sep. 1996.

"Methylation Sepcific PCR" by Herman, et al., Current Protocols in Human Genetics, vol. 2, John Wiley & Sons, Inc., New York, Chichester, Weinhenn,' Brisbane, Singapore, Toronto, 2000.

Bevilacqua et al. Methylation of the hMLH1 promoter but no hMLH1 mutations sporadic gastric carcinomas with high-level microsatellite instability. Int J. Cancer 87, 200-203 (Jan. 2000).

Branch et al. Spontaneous development of drug resistance: Mismatch repair and p53 defects in resistance to cisplatin in human tumor cells. Oncogene 19, 3138-3145 (Jun. 29, 2000).

Esteller et al. HMLH1 promoter hypermethylation is an early event in human endometrial tumorigenesis. Am. J. Pathol. 155, 1767-1772 (Nov. 1999).

Maekawa et al. DNA methylation analysis using bisulfate treatment and PCR-single-strand conformation polymorphism in colorectal cancer showing microsatellite instability. Biochem. Biophys. Res. Comm. 262, 671-676 (Sep. 1999).

\* cited by examiner

Fig. 1

```
   1    acgcttccat ttctttcct agagagaata ttagttttaa agttttccct ctcctaagcc
  61    aattgttcag acatcgtcca ttaaccttt caccatgctc tgattcagat tccgttagta
 121    aagtctgaaa ttcaggtcgc ctaacgcctc tggtcttaat caaaactatc cattcggata
 181    tggtatttat gatctgatta acatctacat cataggagct caacagttcc aagtgaagaa
 241    atcctgaata atgaatgaca ttccaacagt tggggcttac ggccttttct ctcatgtatg
 301    agacgagtcc tgagttctca ccaatcatcc tcaaagtatg ggtcgtggtc agtccaacca
 361    ttctctgcaa gctaagccct gctgtctgca gggactctag gattgccgac atgagcgcac
 421    caacactgaa atgatgagtc aggttgatta tggtcagaag atcttcttgc acctccaact
 481    cagggcctac accgcggata aagaccagga ggtagttctc ataggccaca aaagcctggt
 541    cgtccaaggc aagagaatag gctttaaagt ccctggctcg gttaaaaagc tggttgcgta
 601    gattcctgtc aatgctcagg atcctctgcc ttgtgatatc tggagataag tcaacgcctt
 661    gcaggacgct tacatgctcg gcagtacct ctctcagcaa cacctccatg cactggtata
 721    caaagtcccc ctcacccag ccgcgaccct tcaaggccaa gaggcggcag agcccgaggc
 781    ctgcacgagc agctctctct tcaggagtga aggaggccac gggcaagtcg cctgacgca
 841    gacgctccac cagggccgcg cgctcgccgt ccgccacata ccgctcgtag tattcgtgct
 901    cagcctcgta gtggcgcctg acgtcgcgtt cgcgggtagc tacgatgagg cggcgacaga
 961    ccaggcacag ggccccatcg ccctccggag gctccaccac caaataacgc tgggtccact
1021    cgggccggaa aactagagcc tcgtcgactt ccatcttgct tcttttgggc gtcatccaca
1081    ttctgcggga ggccacaaga gcagggccaa cgttagaaag gccgcaaggg gagaggagga
1141    gcctgagaag cgccaagcac ctcctccgct ctgcgccaga tcacctcagc agaggcacac
1201    aagcccggtt ccggcatctc tgctcctatt ggctggatat ttcgtattcc ccgagctcct
                                                                  5'-t
```

```
        aaaaatgaat taataggaag agtggatagt g-3            (SEQ. ID. NO. 5)
  5'-aaaaatgaat taataggaag agtggatagt g-3'             (SEQ. ID. NO. 4)
     5'-aacgaat taataggaag agcggatagc g-3'             (SEQ. ID. NO. 2)
1261 aaaaacgaac caataggaag agcggacagc gatctctaac gcgcaagcgc atatccttct
```

```
                3'-aca aaatccctcc ctacttctct aa-5'  (SEQ. ID. NO. 6)
         3'-ccc atcatcagca aaatccctcc ctgc-5'       (SEQ. ID. NO. 3)
1321 aggtagcggg cagtagccgc ttcagggagg gacgaagaga cccagcaacc cacagagttg
```

```
1381 agaaatttga ctggcattca agctgtccaa tcaatagctg ccgctgaagg gtggggctgg
1441 atggcgtaag ctacagctga aggaagaacg tgagcacgag gcactgaggt gattggctga
1501 aggcacttcc gttgagcatc tagacgtttc cttggctctt ctggcgccaa aatg 1554
                                                        (SEQ. ID. NO. 1)
```

Fig. 2

```
  1    acgcttccat ttctttct t agagagaata ttagttttaa agttttccct ctcctaagcc
       tgcgaaggta aagaaaagaa tctctcttat aatcaaaatt tcaaagggga gaggattcgg 61    aattgttcag acatcgtcca ttaacccttt caccatgctc tgattcagat tccgttagta
       ttaacaagtc tgtagcaggt aattgggaaa gtggtacgag actaagtcta aggcaatcat 121    aagtctgaaa ttcaggtcgc ctaacgcctc tggtcttaat caaaactatc cattcggata
       ttcagacttt aagtccagcg gattgcggag accagaatta gttttgatag gtaagcctat 181    tggtatttat gatctgatta acatctacat cataggagct caacagttcc aagtgaagaa
       accataaata ctagactaat tgtagatgta gtatcctcga gttgtcaagg ttcacttctt 241    atcctgaata atgaatgaca ttccaacagt tggggcttac ggccttttct ctcatgtatg
       taggacttat tacttactgt aaggttgtca accccgaatg ccggaaaaga gagtacatac 301    agacgagtcc tgagttctca ccaatcatcc tcaaagtatg ggtcgtggtc agtccaacca
       tctgctcagg actcaagagt ggttagtagg agtttcatac ccagcaccag tcaggttggt 361    ttctctgcaa gctaagccct gctgtctgca gggactctag gattgccgac atgagcgcac
       aagagacgtt cgattcggga cgacagacgt ccctgagatc ctaacggctg tactcgcgtg 421    caacactgaa atgatgagtc aggttgatta tggtcagaag atcttcttgc acctccaact
       gttgtgactt tactactcag tccaactaat accagtcttc tagaagaacg tggaggttga 481    cagggcctac accgcggata aagaccagga ggtagttctc ataggccaca aaagcctggt
       gtcccggatg tggcgcctat ttctggtcct ccatcaagag tatccggtgt tttcggacca 541    cgtccaaggc aagagaatag gctttaaagt ccctggctcg gttaaaaagc tggttgcgta
       gcaggttccg ttctcttatc cgaaatttca gggaccgagc caattttttcg accaacgcat 601    gattcctgtc aatgctcagg atcctctgcc ttgtgatatc tggagataag tcaacgcctt
       ctaaggacag ttacgagtcc taggagacgg aacactatag acctctattc agttgcggaa 661    gcaggacgct tacatgctcg ggcagtacct ctctcagcaa cacctccatg cactggtata
       cgtcctgcga atgtacgagc ccgtcatgga gagagtcgtt gtggaggtac gtgaccatat 721    caaagtcccc ctcaccccag ccgcgaccct tcaaggccaa gaggcggcag agcccgaggc
       gtttcagggg gagtggggtc ggcgctggga agttccggtt ctccgccgtc tcgggctccg 781    ctgcacgagc agctctctct tcaggagtga aggaggccac gggcaagtcg ccctgacgca
       gacgtgctcg tcgagagaga agtcctcact tcctccggtg cccgttcagc gggactgcgt
```

Fig. 3-1

```
841    gacgctccac caggggccgcg cgctcgccgt ccgccacata ccgctcgtag tattcgtgct
       ctgcgaggtg gtcccggcgc gcgagcggca ggcggtgtat ggcgagcatc ataagcacga 901    cagcctcgta gtggcgcctg acgtcgcgtt cgcgggtagc tacgatgagg cggcgacaga
       gtcggagcat caccgcggac tgcagcgcaa gcgcccatcg atgctactcc gccgctgtct 961    ccaggcacag ggccccatcg ccctccggag gctccaccac caaataacgc tgggtccact
       ggtccgtgtc ccggggtagc gggaggcctc cgaggtggtg gtttattgcg acccaggtga 1021   cgggccggaa aactagagcc tcgtcgactt ccatcttgct tcttttgggc gtcatccaca
       gcccggcctt ttgatctcgg agcagctgaa ggtagaacga agaaaacccg cagtaggtgt 1081   ttctgcggga ggccacaaga gcagggccaa cgttagaaag gccgcaaggg gagaggagga
       aagacgccct ccggtgttct cgtcccggtt gcaatctttc cggcgttccc ctctcctcct 1141   gcctgagaag cgccaagcac ctcctccgct ctgcgccaga tcacctcagc agaggcacac
       cggactcttc gcggttcgtg gaggaggcga gacgcggtct agtggagtcg tctccgtgtg 1201   aagcccggtt ccggcatctc tgctcctatt ggctggatat ttcgtattcc ccgagctcct
       ttcgggccaa ggccgtagag acgaggataa ccgacctata aagcataagg ggctcgagga 1261   aaaaacgaac caataggaag agcggacagc gatctctaac gcgcaagcgc atatccttct
       tttttgcttg gttatccttc tcgcctgtcg ctagagattg cgcgttcgcg tataggaaga 1321   aggtagcggg cagtagccgc ttcagggagg gacgaagaga cccagcaacc cacagagttg
       tccatcgccc gtcatcggcg aagtccctcc ctgcttctct gggtcgttgg gtgtctcaac 1381   agaaatttga ctggcattca agctgtccaa tcaatagctg ccgctgaagg gtggggctgg
       tctttaaact gaccgtaagt tcgacaggtt agttatcgac ggcgacttcc caccccgacc 1441   atggcgtaag ctacagctga aggaagaacg tgagcacgag gcactgaggt gattggctga
       taccgcattc gatgtcgact tccttcttgc actcgtgctc cgtgactcca ctaaccgact 1501   aggcacttcc gttgagcatc tagacgtttc cttggctctt ctggcgccaa aatg    1554
       tccgtgaagg caactcgtag atctgcaaag gaaccgagaa gaccgcggtt ttac
                                                           SEQ. ID. NO. 1
```

METHODS AND COMPOSITIONS FOR DETECTING CANCERS ASSOCIATED WITH METHYLATION OF *HMLH1* PROMOTER DNA

CROSS REFERENCE TO RELATED APPLICATIONS

This application is a divisional of U.S. patent application Ser. No. 09/957,661, filed on Sep. 20, 2001 now U.S. Pat. No. 6,858,388, which claims priority to U.S. Provisional Application Ser. No. 60/234,087, filed Sep. 20, 2000, the contents of each of which are incorporated herein by reference in their entirety.

This invention was made, at least in part, with government support under National Institutes of Health Grant Nos: KO8 CA77676, RO1 CA67409 and RO1 CA72160. The U.S. government has certain rights in the invention.

BACKGROUND

In 2001, over 1.2 million new cases of human cancer will be diagnosed and over 0.5 million people will die from cancer (American Cancer Society estimate). Despite this, more people than ever are living with and surviving cancer. In 1997, for example, approximately 8.9 million living Americans had a history of cancer (National Cancer Institute estimate). People are more likely to survive cancer if the disease is diagnosed at an early stage of development, since treatment at that time is more likely to be successful. Early detection depends upon availability of high-quality methods. Such methods are also useful for determining patient prognosis, selecting therapy, monitoring response to therapy and selecting patients for additional therapy. Consequently, there is a need for cancer diagnostic methods that are specific, accurate, minimally invasive, technically simple and inexpensive.

Colorectal cancer (i.e., cancer of the colon or rectum) is one particularly important type of human cancer. Colorectal cancer is the second most common cause of cancer mortality in adult Americans (Landis, et al., 1999, CA Cancer J Clin, 49: 8-31). Approximately 40% of individuals with colorectal cancer die. In 2001, it is estimated that there will be 135,400 new cases of colorectal cancer (98,200 cases of colon and 37,200 cases of rectal cancer) and 56,700 deaths (48,000 colon cancer and 8,800 rectal cancer deaths) from the disease (American Cancer Society). As with other cancers, these rates can be decreased by improved methods for diagnosis.

Although methods for detecting colorectal cancer exist, the methods are not ideal. Digital rectal exams (i.e., manual probing of rectum by a physician), for example, although relatively inexpensive, are unpleasant and can be inaccurate. Fecal occult blood testing (i.e., detection of blood in stool) is nonspecific because blood in the stool has multiple causes. Colonoscopy and sigmoidoscopy (i.e., direct examination of the colon with a flexible viewing instrument) are both uncomfortable for the patient and expensive. Double-contrast barium enema (i.e., taking X-rays of barium-filled colon) is also an expensive procedure, usually performed by a radiologist.

Additional methods for detecting colorectal cancer require tissue from the tumor. In order to use these methods, growth of the tumor must have progressed far enough that the tumor is visible. A second disadvantage of these methods is that they require a tissue biopsy to be taken from the tumor.

Because of the disadvantages of existing methods for detecting colorectal cancer, new methods are needed.

SUMMARY OF THE INVENTION

In accordance with the present invention, new methods are provided for detection of cancers associated with methylation of hMLH1 promoter DNA in a subject. In one aspect, the method comprises assaying for the presence of methylated hMLH1 promoter DNA in a bodily fluid from a subject. Preferably, the sample is blood, serum, plasma, a blood-derived fraction, stool, colonic effluent or urine. Preferably, such method comprises reacting DNA from the sample with a chemical compound that converts non-methylated cytosine bases (also called "conversion-sensitive" cytosines), but not methylated cytosine bases, to a different nucleotide base. In a preferred embodiment, the chemical compound is sodium bisulfite, which converts unmethylated cytosine bases to uracil. The compound-converted DNA is then amplified using a methylation-sensitive polymerase chain reaction (MSP) employing primers that amplify the compound-converted DNA template if cytosine bases within CpG dinucleotides of the DNA from the sample are methylated. Production of a PCR product indicates that the subject has a cancer associated with methylation of hMLH1 promoter DNA.

In another aspect, the present invention provides a detection method for prognosis of a cancer in a subject known to have or suspected of having a cancer associated with methylation of hMLH1 promoter DNA, referred to hereinafter as an "hMLH1 methylation-associated cancer". Such method comprises assaying for the presence of methylated hMLH1 promoter DNA in a bodily fluid from the subject. In certain cases, presence of the methylated hMLH1 promoter DNA in the bodily fluid indicates that the subject is a good candidate for a particular therapy. In other cases, presence of the methylated hMLH1 promoter DNA in the bodily fluid indicates that the hMLH1 methylation associated cancer has a poor prognosis or the subject is a candidate for more aggressive therapy.

In another aspect, the present invention provides a method for monitoring over time the status of an hMLH1 methylation-associated cancer in a subject. The method comprises assaying for the presence of methylated hMLH1 promoter DNA in a bodily fluid taken from the subject at a first time and in a corresponding bodily fluid taken from the subject at a second time. Absence of methylated hMLH1 promoter DNA from the bodily fluid taken at the first time and presence of methylated hMLH1 promoter DNA in the bodily fluid taken at the second time indicates that the cancer is progressing. Presence of methylated hMLH1 promoter DNA in the bodily fluid taken at the first time and absence of methylated hMLH1 promoter DNA from the bodily fluid taken at the second time indicates that the cancer is regressing.

In another aspect the present invention provides a method for evaluating therapy in a subject suspected of having or having an hMLH1 methylation-associated cancer. The method comprises assaying for the presence of methylated hMLH1 promoter DNA in a bodily fluid taken from the subject prior to therapy and a corresponding bodily fluid taken from the subject during or following therapy. Loss of methylated hMLH1 promoter DNA in the sample taken after or during therapy as compared to the presence of methylated hMLH1 promoter DNA in the sample taken before therapy is indicative of a positive effect of the therapy on cancer regression in the treated subject.

The present invention also provides nucleotide primer sequences for use in the methylation-sensitive PCR assay.

BRIEF DESCRIPTION OF THE FIGURES

FIG. 2. Sequence level illustration of part of the hMLH1 promoter (i.e. the Watson strand, designed as SEQ ID NO: 1), showing location and sequence of primers. Primers are in bold type (SEQ ID NOs: 2-6). The numbering scheme is based on the GenBank sequence entry U83845 (Kane, et al., 1997, Cancer Res, 57:808-11).

FIG. 3. Double-stranded DNA sequence of the hMLH1 promoter (GenBank accession number U83845) (Kane, et al., 1997, Cancer Res, 57:808-11). The top strand is designed as SEQ ID NO: 1, while the bottom strand is the complementary sequence of SEQ ID NO: 1.

DETAILED DESCRIPTION OF THE INVENTION

The present invention provides a method for detecting cancers in a subject that are associated with methylation of hMLH1 promoter DNA in a bodily fluid from the subject. The preferred bodily fluid is blood, serum, plasma, blood-derived fraction, stool, colonic effluent or urine.

DEFINITIONS

Herein, "Watson strand" refers to one specific strand of a double-stranded DNA. Herein, the Watson strand of the hMLH1 promoter is the same strand of DNA that contains the coding sequence of the hMLH1 gene. The RNA that is transcribed from the hMLH1 gene is identical in sequence to the coding sequence of the HMLH1 gene, except that thymine (T) bases in the DNA coding strand sequence are replaced by uracil (U) bases in the RNA. The Watson strand of the DNA is the strand of the DNA that is conventionally shown when a single strand of a double-stranded DNA gene sequence is pictured.

Herein, "Crick strand" refers to one specific strand of a double-stranded DNA. Herein, the Crick strand of the hMLH1 promoter is the same strand of DNA that contains the noncoding sequence of the hMLH1 gene. The RNA that is transcribed from the hMLH1 gene is complementary in sequence to the noncoding sequence of the hMLH1 gene (U bases in the RNA are complementary to adenine bases (A) in the noncoding sequence of the DNA). The Crick strand of the DNA is the strand of the DNA that is, by convention, complementary to the single strand of DNA shown when a double-stranded DNA gene sequence is pictured.

Herein, "conversion-sensitive cytosine" refers to cytosine (C) bases in DNA that are unmethylated (i.e., are not 5-methylcytosine).

Herein, "compound-converted DNA" refers to DNA that has been treated or reacted with a chemical compound that converts unmethylated C bases in DNA to a different nucleotide base. Herein, one such compound is sodium bisulfite, which converts unmethylated C to U. If DNA that contains conversion-sensitive cytosine is treated with sodium bisulfite, the compound-converted DNA will contain U in place of C. If the DNA which is treated with sodium bisulfite contains only methylcytosine, the compound-converted DNA will not contain uracil in place of the methylcytosine.

For example, the diagram below shows how sodium bisulfite treatment results in sequence changes within a DNA strand, dependent upon whether C bases in the DNA are methylated or not. Diagram I below shows a single-stranded DNA sequence. Two C bases within the sequence shown in I are part of CpG dinucleotides (i.e., the base immediately 3' of the C is G). These two C bases are shaded in diagram I. Four other C bases are not part of CpG dinucleotides (i.e., the base immediately 3' of the C is A, C or T). These four C bases are underlined in diagram I.

In the case that the two C bases in diagram I that are part of CpG dinucleotides (the shaded C bases) are methylate (i.e., are 5-methylcytosine bases), sodium bisulfite treatment of the DNA strand shown in diagram I will produce the DNA sequence shown in diagram II. Diagram II shows that only C bases that are unmethylated are converted to U by sodium bisulfite. C bases that are methylated (i.e., the two shaded C bases in diagram I) are not converted to U, nor to any other base, by sodium bisulfite.

In the case that the two C bases in diagram I that are part of CpG dinucleotides (the shaded C bases) are not methylated, sodium bisulfite treatment of the DNA strand shown in diagram I will produce the DNA sequence shown in diagram III. Diagram III shows that all C bases in diagram I are converted to U by sodium bisulfite. Only C bases that are methylated are protected from conversion to U by sodium bisulfite. Since all C bases in diagram I (C bases that are part of CpG dinucleotides, and C bases that are not part of CpG dinucleotides) are unmethylated in this scenario, all C bases are converted to U, as shown in diagram III.

Herein, "compound-converted template sequence" refers to a region of the hMLH1 promoter DNA that is rich in CpG dinucleotide sequences (i.e. 2 or more CpG dinucleotides), that has been treated with a chemical compound that converts unmethylated C bases in DNA to a different nucleotide base, and that is amplified by a methylation-sensitive polymerase chain reaction (MSP). Herein, the compound-converted template sequence is single-stranded and is either the Watson or Crick strand of the DNA.

Herein, "target sequence" refers to regions of the compound-converted template sequence from which the primers used in the MSP are derived. These target sequences are located at both ends of the compound-converted template sequence that is amplified by the MSP. Target sequences are between 8 and 50 nucleotides in length. Primers derived from the target sequences at both ends of a compound-converted template sequence will amplify the compound-converted template sequence in a MSP reaction (see below).

Herein, the "second target sequence" is at the 3' end of the compound-converted template sequence. The second target sequence contains at least one CpG dinucleotide (if C in the CpG dinucleotides in the DNA treated with sodium bisulfite is methylated) or at least one UpG dinucleotide (if C in the CpG dinucleotides in the DNA treated with sodium bisulfite is not methylated). The second target sequence also contains at least one U that is immediately 5' of an A, T or C base.

During the first round of the MSP, the reverse primer (see below) anneals to the second target sequence of the compound-converted template sequence. The reverse primer is complementary in sequence to the second target sequence of the compound-converted template sequence. After the reverse primer anneals, the 3' end of the reverse primer is extended in the 5' direction by the polymerase present in the MSP. Extension of the reverse primer by the polymerase is called herein, the "first round" of the MSP.

Herein, the "first target sequence" is at the 5' end of the compound-converted template sequence. The first target sequence contains at least one CpG dinucleotide (if C in the CpG dinucleotides in the DNA treated with sodium bisulfite is methylated) or at least one UpG dinucleotide (if C in the CpG dinucleotides in the DNA treated with sodium bisulfite is not methylated). The first target sequence also contains at least one U that is immediately 5' of an A, T or C base.

During the second round of the MSP, the forward primer (see below) anneals to the 3' end of the extended reverse primer that is the product of the first round of the MSP. The forward primer is identical in sequence to the "first target sequence," except that U bases are replaced by T bases. Thus, the sequence of the forward primer is "substantially identical" to the first target sequence. After the forward primer anneals, the 3' end of the forward primer is extended in the 5' direction by the polymerase present in the MSP. Extension of the forward primer by the polymerase is called herein, the "second round" of the MSP. Addition cycles of both the first round step and the second round step of the MSP gives rise to the MSP product whose presence is determinative of methylation in the hMLH1 promoter (see discussion below).

Herein, "methylation-sensitive PCR" (MSP) refers to a polymerase chain reaction in which amplification of the compound-converted template sequence is performed. Two sets of primers are designed for use in MSP. Each set of primers comprises a forward primer and a reverse primer. One set of primers, called methylation-specific primers (see below), will amplify the compound-converted template sequence if C bases in CpG dinucleotides within the hMLH1 promoter DNA are methylated. Another set of primers, called unmethylation-specific primers (see below), will amplify the compound-converted template sequences if C bases in CpG dinucleotides within the hMLH1 promoter DNA are not methylated.

Herein, "methylation-specific primers" are primers that direct amplification of a compound-converted template sequence where C bases within CpG dinucleotides of the first target sequence and the second target sequence are methylated.

Herein, "unmethylation-specific primers" are primers that direct amplification of a compound-converted template sequence where C bases within CpG dinucleotides of the first target sequence and the second target sequence are not methylated.

Herein, "reverse primer" refers to a primer for MSP that is located at the 3' end of the compound-converted template sequence and anneals to the second target sequence within the compound-converted template sequence. The reverse primer is complementary in sequence to the second target sequence of the compound-converted template sequence. The reverse primer is also identical to the reverse complement of the second target sequence. The sequence of the reverse primer contains C bases that are complementary to G bases within the second target sequence, G bases that are complementary to C bases, T bases that are complementary to A bases, and A bases that are complementary to both T and U bases in the second target sequence.

Herein, "forward primer" refers to a primer for MSP that is located at the 5' end of the compound-converted template sequence and anneals to the 3' end of the product of the first round of the MSP. The forward primer is identical in sequence to the first target sequence, except that U bases in the second target sequence are replaced by T bases in the forward primer. Thus, the sequence of the forward primer is "substantially identical" to the first target sequence.

Herein, "blood-derived fraction" refers to a component or components of whole blood. Whole blood comprises a liquid portion (i.e., plasma) and a solid portion (i.e., blood cells). The liquid and solid portions of blood are each comprised of multiple components; e.g., different proteins in plasma or different cell types in the solid portion. One of these components or a mixture of any of these components is a blood-derived fraction as long as such fraction is missing one or more components found in whole blood.

Genetic Changes in Colon Cancer

A number of human cancers are associated with genetic changes in DNA mismatch repair genes. DNA mismatch repair genes encode proteins that correct errors in DNA that are made when DNA polymerases insert an incorrect nucleotide base at a specific position in the DNA sequence during replication of the DNA. Defects in DNA mismatch repair genes result in cellular mutation rates at least 100-times higher than in cells with intact DNA mismatch repair genes (Modrich and Lahue, 1996, Annu Rev Biochem, 65: 101-33; Thomas, et al., 1996, Mutat Res, 350: 201-5).

One manifestation of the high mutation rate associated with defects in DNA mismatch repair genes is instability of DNA microsatellite sequences. Microsatellite sequences are comprised of nucleotide motifs 1-4 nucleotides in length that are repeated, possibly 100,000 times, in the human genome. Defects in DNA mismatch repair genes result in differences in the lengths of the nucleotide motif repeats in cancer cells as compared to normal cells. The process that leads to the repeat length differences is called microsatellite instability (MSI) and is found in a number of human cancer types.

A number of different DNA mismatch repair genes exist in humans. Germ-line mutation and inactivation of any of these commonly give rise to familial MSI colon cancers, known as hereditary nonpolyposis colon cancers (Marra and Boland, 1995, J Natl Cancer Inst, 87: 1114-25; Lynch and Smyrk, 1996, Cancer, 78: 1149-67). More common than the inherited type are colorectal cancers that arise sporadically (i.e., arise in an individual but are not inherited). In certain sporadic colorectal cancers, genetic changes in one particular DNA mismatch repair gene, hMLH1, are prominent.

Although alterations in the hMLH1 gene are frequent in sporadic colorectal cancer, only a small percentage of these alterations are genetic mutations that change the DNA sequence of the hMLH1 gene. Rather, the hMLH1 genes in these sporadic cancers more often display epigenetic changes, specifically, changes in their DNA methylation patterns. In mammalian cells, DNA methylation comprises addition of a methyl group to the 5-carbon position of cytosine (C) nucleotide bases to form 5-methylcytosine (5mC) or methylcytosine. Only cytosines located 5' to guanines (G) in CpG dinucleotides are methylated in mammalian cells, but not all CpG dinucleotides are methylated. The pattern of methylation (i.e., whether a particular CpG dinucleotide is methylated or not) is relatively constant in cells (i.e., is maintained as cells divide), but can change under various circumstances. In such cases, the changed methylation pattern becomes relatively constant and is maintained.

One circumstance in which methylation patterns in cells can change is in certain human cancers. In such cancers, the methylation status (whether methylated or unmethylated) of certain CpG dinucleotides changes. In 10% of colon cancers (and 90% of MSI colon cancers), for example, there is methylation of C bases in CpG dinucleotides in the promoter region of the hMLH1 gene. Ten to fifteen percent of gastric cancers also have methylation of C bases in CpG dinucleotides in the hMLH1 promoter. Methylated C bases in CpG dinucleotides of hMLH1 promoter DNA are also found in endometrial cancer, ovarian cancer and in precancerous colon adenomas.

Once established, the methylation of C bases within CpG dinucleotides in cancers is stable. These C bases are not methylated in non-cancerous cells (Kane, et al., 1997, Cancer Res, 57: 808-11; Veigl, et al., 1998, Proc Natl Acad Sci USA, 95: 8698-702; Herman, et al., 1998, Proc Natl Acad Sci USA, 95: 6870-5). Methylation of C bases within CpG dinucleotides within nucleotides 1264 to 1354 of the hMLH1 promoter (as numbered in GenBank sequence entry U83845; FIGS. 2 and 3 of this document) are correlated with lack of expression of the hMLH1 gene in colorectal cancer (Deng, et al., 1999, Cancer Res, 59: 2029-33).

Detection of Changed Methylation in hMLH1 Promoter DNA

The hMLH1 promoter DNA, in its methylated state, is thus a cancer-specific modification that can serve as a target for detection using assay methods. One assay for detecting such methylated nucleotides is based on treatment of genomic DNA with a chemical compound which converts non-methylated C, but not methylated C (i.e., 5mC), to a different nucleotide base. One such compound is sodium bisulfite, which converts C, but not 5mC, to U. Methods for bisulfite treatment of DNA are known in the art (Herman, et al., 1996, Proc Natl Acad Sci USA, 93: 9821-6; Herman and Baylin, 1998, Current Protocols in Human Genetics, N. E. A. Dracopoli, ed., John Wiley & Sons, 2: 10.6.1-10.6.10). When DNA that contains unmethylated C nucleotides is treated with sodium bisulfite to give compound-converted DNA, the sequence of that DNA is changed (C→U). Detection of U in the DNA is indicative of an unmethylated C.

The different nucleotide base (e.g., U) present in compound-converted DNA sequences can be detected in a variety of ways. One method of detecting U in compound-converted DNA sequences is a method called "methylation sensitive PCR" (MSP). In MSP, one set of primers (i.e., a set of primers comprises a forward and a reverse primer) amplifies the compound-converted template sequence if C bases in CpG dinucleotides within the hMLH1 promoter DNA are methylated. This set of primers is called "methylation-specific primers." Another set of primers amplifies the compound-converted template sequence if C bases in CpG dinucleotides within the hMLH1 promoter DNA are not methylated. This set of primers is called "unmethylation-specific primers."

Two separate PCR reactions are then run. Both reactions use the compound-converted DNA from bodily fluid. In one of the reactions, methylation-specific primers are used. In the case where C within CpG dinucleotides of the target sequence of the DNA are methylated, the methylation-specific primers will amplify the compound-converted template sequence in the presence of a polymerase and an MSP product will be produced. If C within CpG dinucleotides of the target sequence of the DNA are not methylated, the methylation-specific primers will not amplify the compound-converted template sequence in the presence of a polymerase and an MSP product will not be produced.

In the other reaction, unmethylation specific primers are used. In the case where C within CpG dinucleotides of the target sequence of the DNA are unmethylated, the unmethylation specific primers will amplify the compound-converted template sequence in the presence of a polymerase and an MSP product will be produced. If C within CpG dinucleotides of the target sequence of the DNA are methylated, the unmethylation-specific primers will not amplify the compound-converted template sequence in the presence of a polymerase and an MSP product will not be produced.

Selection of Primers for MSP

Primers are derived from target sequences at the ends of the compound-converted hMLH1 promoter template sequence. Herein, "derived from" means that the sequences of the primers are chosen such that the primers amplify the compound-converted template sequence, which includes the target sequences, in an MSP reaction. The second target sequence is at the 3' end of the compound-converted template sequence. The first target sequence is at the 5' end of the compound-converted template sequence. Target sequences are between 8 and 50 nucleotides in length, preferably from 25 to 32 nucleotides in length. The target sequences contain at least one CpG dinucleotide, preferably two or more CpG dinucleotides (if C in the CpG dinucleotides in the DNA treated with sodium bisulfite is methylated), or at least one UpG dinucleotide, preferably two or more UpG dinucleotides (if C in the CpG dinucleotides in the DNA treated with sodium bisulfite is not methylated). Preferably, one of the CpG or UpG dinucleotides is located at the 5' end of the second target sequence. Preferably one of the CpG or UpG dinucleotides is located at the 3' end of the first target sequence. The target sequences also contain at least one U that is immediately 5' of an A, T or C base.

Each primer comprises a single-stranded DNA fragment which is at least 8 nucleotides in length. Preferably, the primers are less than 50 nucleotides in length, more preferably from 15 to 35 nucleotides in length. The sequences of the primers are derived from the target sequences. The reverse primer is complementary in sequence to the second target sequence of the compound-converted template sequence. The reverse primer is also identical to the reverse complement of the second target sequence. The sequence of the reverse primer contains C bases that are complementary to G bases within the second target sequence, G bases that are complementary to C bases, T bases that are complementary to A bases, and A bases that are complementary to both T and U bases in the second target sequence. The forward primer is identical in sequence to the first target sequence, except that U bases in the first target sequence are replaced by T bases in the forward primer. Thus, the sequence of the forward primer is substantially "identical" to the first target sequence.

Because the compound-converted template sequence can be either the Watson strand or the Crick strand of the double-stranded DNA that is treated with sodium bisulfite, the sequences of the primers is dependent upon whether the Watson or Crick compound-converted template sequence is chosen to be amplified in the MSP. Either the Watson or Crick strand can be chosen to be amplified.

One set of primer sequences (a set of primers comprises a forward primer and a reverse primer), called methylation-specific primers, is chosen such that the primers amplify the compound-converted template sequence when the compound-converted template sequence contains one or more CpG dinucleotides. Another set of primer sequences, called unmethylation-specific primers, is chosen such that the primers amplify the compound-converted template sequence when the compound-converted template sequence contains one or more UpG dinucleotides.

The compound-converted template sequence, and therefore the product of the MSP reaction, can be between 20 to 2000 nucleotides in length, preferably between 50 to 500 nucleotides in length, more preferably between 80 to 150 nucleotides in length. Preferably, the methylation-specific primers result in an MSP product of a different length than the MSP product produced by the unmethylation-specific primers.

Samples and Isolation of DNA Therefrom

DNA which is used as the template in the MSP is obtained from a subject suspected of or known to have, or to have had, an hMLH1 methylation-associated cancer. Alternatively, the template DNA is from a subject who is undergoing a routine screening and who is not necessarily suspected of having an hMLH1 methylation-associated cancer. This DNA is obtained from a bodily fluid. Examples of preferred bodily fluids are blood, serum, plasma, a blood-derived fraction, stool, colonic effluent or urine. Other body fluids can also be used. Because they can be easily obtained from the subject and can be used to screen for multiple diseases, blood or blood-derived fractions are especially useful. It has been shown that DNA alterations in colorectal cancer patients can be detected in the blood of subjects (Hibi, et al., 1998, Cancer Res, 58: 1405-7).

Blood-derived fractions can comprise blood, serum, plasma, or other fractions. For example, a cellular fraction can be prepared as a "buffy coat" (i.e., leukocyte-enriched blood portion) by centrifuging 5 ml of whole blood for 10 min at 800 times gravity at room temperature. Red blood cells sediment most rapidly and are present as the bottom-most fraction in the centrifuge tube. The buffy coat is present as a thin creamy white colored layer on top of the red blood cells. The plasma portion of the blood forms a layer above the buffy coat. Fractions from blood can also be isolated in a variety of other ways. One method is by taking a fraction or fractions from a gradient used in centrifugation to enrich for a specific size or density of cells.

DNA is then isolated from samples from the bodily fluids. Procedures for isolation of DNA from such samples are well known to those skilled in the art. Commonly, such DNA isolation procedures comprise lysis of any cells present in the samples using detergents, for example. After cell lysis, proteins are commonly removed from the DNA using various proteases. RNA is removed using RNase. The DNA is then commonly extracted with phenol, precipitated in alcohol and dissolved in an aqueous solution.

Methylation-Sensitive PCR (MSP)

Isolated DNA is reacted with a compound that converts umethylated cytosine (C) bases in the DNA to another base. Preferably, the compound is sodium bisulfite, which converts umethylated C to uracil (U). Portions of the compound-converted DNA is used in two different MSP reactions with different primers. In each MSP reaction, the primers comprise a forward primer and a reverse primer. In one of the MSP reactions, methylation-specific primers are used. In another of the MSP reactions, unmethylation-specific primers are used. Conditions for the MSP reactions are well known to those skilled in the art and are described in more detail in Example 5.

A variety of methods can be used to determine if an MSP product has been produced in a reaction assay. One way to determine if an MSP product has been produced in the reaction is to analyze a portion of the reaction by agarose gel electrophoresis. For example, a horizontal agarose gel of from 0.6 to 2.0% agarose is made and a portion of the MSP reaction mixture is electrophoresed through the agarose gel. After electrophoresis, the agarose gel is stained with ethidium bromide. MSP products are visible when the gel is viewed during illumination with ultraviolet light. By comparison to standardized size markers, it is determined if the MSP product is of the correct expected size.

Other methods can be used to determine whether a product is made in an MSP reaction. One such method is called "real-time PCR." Real-time PCR utilizes a thermal cycler (i.e., an instrument that provides the temperature changes necessary for the PCR reaction to occur) that incorporates a fluorimeter (i.e. an instrument that measures fluorescence). The real-time PCR reaction mixture also contains a reagent whose incorporation into a product can be quantified and whose quantification is indicative of copy number of that sequence in the template. One such reagent is a fluorescent dye, called SYBR Green I (Molecular Probes, Inc.; Eugene, Oreg.) that preferentially binds double-stranded DNA and whose fluorescence is greatly enhanced by binding of double-stranded DNA. When a PCR reaction is performed in the presence of SYBR Green I, resulting DNA products bind SYBR Green I and fluorescence. The fluorescence is detected and quantified by the fluorimeter. Such technique is particularly useful for quantification of the amount of template in PCR reaction.

Other Methods for Detecting Methylated hMLH1 Promoter DNA Sequences

A modification of MSP is that primers for use in MSP are designed and chosen such that products of the MSP reaction are susceptible to digestion by restriction endonucleases, dependent upon whether the compound-converted template sequence contains CpG dinucleotides or UpG dinucleotides.

Another technique referred to as MS-SnuPE, uses compound-converted DNA as a template in a primer extension reaction wherein the primers used produce a product, dependent upon whether the compound-converted template contains CpG dinucleotides or UpG dinucleotides.

Another technique is to directly sequence the product resulting from an MSP reaction to determine if the compound-converted template sequence contained CpG dinucleotides or UpG dinucleotides.

Another technique for detecting methylated hMLH1 promoter DNA sequences uses restriction endonucleases called "methylation-sensitive" restriction endonucleases to treat the DNA isolated from the bodily fluid of a subject. The restriction endonuclease-treated DNA is then used as a template in a PCR reaction. Herein, methylation-sensitive restriction endonucleases recognize and cleave a specific sequence within the DNA if C bases within the recognition sequence are not methylated. If C bases within the recognition sequence of the restriction endonuclease are methylated, the DNA will not be cleaved. One such methylation-sensitive restriction endonuclease is Hpa II. Other such methylation-sensitive restriction endonucleases exist and are known in the art. In this technique, a recognition sequence for a methylation-sensitive restriction endonuclease is located within the template DNA, at a position between the forward and reverse primers used for the PCR reaction. In the case that a C base within the methylation-sensitive restriction endonuclease recognition sequence is not methylated, the endonuclease will cleave the DNA template and a PCR product will not be formed when the DNA is used as a template in the PCR reaction. In the case that a C base within the methylation-sensitive restriction endonuclease recognition sequence is methylated, the endonuclease will not cleave the DNA template and a PCR product will be formed when the DNA is used as a template in the PCR reaction. Therefore, methylation of C bases can be determined by the absence or presence of a PCR product (Kane, et al., 1997, Cancer Res, 57: 808-11). No sodium bisulfite is used in this technique.

Subjects from which Samples are Obtained

An important aspect of the invention is that DNA that is assayed in the MSP comes from human subjects that are suspected of having, has, or is known to have had a cancer associated with methylation of hMLH1 promoter DNA. Alternatively, the DNA comes from a subject who is undergoing routine screening and who is not necessarily suspected of having an hMLH1 associated cancer.

Detection of methylation of hMLH1 promoter DNA in samples from subjects that are not known to have had a cancer associated with methylation of hMLH1 promoter DNA can aid in diagnosis of such a cancer in the subject. The MSP assay of this invention can be used by itself, or in combination with other various assays, to improve the sensitivity and/or specificity of detection of the hMLH1 methylation associated cancer. Preferably, such detection is made at an early stage in the development of cancer, so that treatment is more likely to be effective.

In addition to diagnosis, detection of hMLH1 promoter DNA methylation in a sample from a subject not known to have had a cancer, can be prognostic for the subject (i.e., indicate the probable course of the disease). For example, cancers having a high probability of a favorable outcome in the subject may be associated with methylated hMLH1 promoter DNA. Alternatively, the presence of methylated hMLH1 promoter DNA in certain bodily fluids, such as blood, can indicate that the prognosis is poor. The prognostic potential of the method of the present invention may be particularly high if detection of hMLH1 promoter methylation is indicative of a particular stage of the cancer or is associated with other characteristics of a cancer wherein the other characteristics are prognostic.

Detection of hMLH1 promoter DNA methylation in samples from subjects can also be used to select a particular therapy or therapies which are particularly effective against the cancer in the subject, or to exclude therapies that are not likely to be effective. For example, colon cancer patients receiving adjuvant chemotherapy with 5-Fluorouracil had a much better survival rate if their tumors were MSI colon cancers (Watanabe, et al., 2001, N Engl J Med, 344: 1196-206). Ninety percent of MSI colon cancers have methylated hMLH1 promoter DNA. Information of this type could also result in improved therapy design and, potentially, improved survival for the patient.

Detection of methylation of hMLH1 promoter DNA in samples from subjects that are known to have, or to have had, a cancer associated with methylation of hMLH1 promoter DNA is also useful. For example, the present methods can be used to identify subjects for whom therapy is or is not working. One or more bodily fluids are taken from the subject prior to and following therapy and assayed for the presence of methylated hMLH1 promoter DNA. A finding that the methylated hMLH1 promoter DNA is present in the sample taken prior to therapy and absent after therapy would indicate that the therapy is effective and need not be altered. In those cases where the methylated hMLH1 promoter DNA is present in the sample taken before therapy and in the sample taken after therapy, it may be desirable to alter the therapy to increase the likelihood that the cancer will be eradicated in the subject. Thus, the present method could obviate the need to perform more invasive procedures which are used to determine a patient's response to therapy.

Cancers frequently recur following therapy in patients with advanced cancers. In this and other instances, the present detection methods are useful for monitoring over time the status of an hMLH1 methylation associated cancer. For subjects in which cancer is progressing, methylated hMLH1 promoter DNA may be absent from some or all bodily fluids when the first sample is taken and then appear in one or more bodily fluids when the second sample is taken. For subjects in which cancer is regressing, methylated hMLH1 promoter DNA may be present in one or a number of bodily fluids when the first sample is taken and then be absent in some or all of these bodily fluids when the second sample is taken.

EXAMPLES

The following examples are for purposes of illustration only and are not intended to limit the scope of the invention as defined in the claims which are appended hereto.

Example 1

Selection of Primers

To attain maximal sensitivity and specificity, primers for hMLH1 MSP were designed that, following bisulfite conversion, selectively amplified compound-converted templates derived from either methylated (i.e., containing CpG dinucletides) or unmethylated (i.e., containing UpG dinucletides) versions of sequences contained within base pairs 1264 to 1354 of the hMLH1 promoter DNA of GenBank entry U83845 (FIG. 2), a region whose methylation status has been demonstrated to invariably correlate with hMLH1 expression in colon cancer (Deng, et al., 1999, Cancer Res, 59: 2029-33). The primers annealed to a region of the hMLH1 promoter sequence that contained a total of five CpG dinucleotides with at least one CpG dinucleotide placed at the 3' end of each primer to maximize discrimination between methylated and umethylated alleles after sodium bisulfite treatment. (FIG. 2.). To further enhance the discrimination between products amplified by the primer sets that amplified compound-converted templated sequences derived from methylated versus unmethylated hMLH1 promoter DNA, the primers were designed to generate MSP products that varied in size by 11 bp (102 bp vs. 91 bp). The short size of these MSP products also increased the utility of these primers for determining the methylation status of the hMLH1 promoter in samples of paraffin-embedded, formalin-fixed tumor tissues. The methylated and unmethylated primer pair sequences were as shown in Table 1 below. The primer pairs were purchased from Sigma-Genosys (The Woodlands, Tex.).

TABLE 1

Primers for amplification of the
Watson strand in MSP PCR

| Primer name | Sequence (5' → 3') | SEQ. ID. NO. |
|---|---|---|
| Methyl specific forward primer 1 | AACGAATTAATAGGAAGAGCGGATAGCG | 2 |
| Methyl specific reverse primer 1 | CGTCCCTCCCTAAAACGACTACTACCC | 3 |
| Unmethyl specific forward primer 1 | AAAAATGAATTAATAGGAAGAGTGGATAGTG | 4 |
| Unmethyl specific forward primer 2 | TAAAAATGAATTAATAGGAAGAGTGGATAGTG | 5 |
| Unmethyl specific reverse primer 1 | AATCTCTTCATCCCTCCCTAAAACA | 6 |

The cell lines RKO, SW480, Vaco-5, and Vaco-457 were used. RKO cells were obtained from M. Brattain at the Univesity of Texas Health Science Center, San Antonio, Tex. SW480 cells were obtained from the American Type Culture Collection, 10801 University Boulevard, Manassas, Va. 20110-2209. The Vaco cell lines were established from colon cancers as described previously (Markowitz, et al., 1995, Science, 268: 1336-8; Willson, et al., 1987, Cancer Res, 47: 2704-13). Cells were cultured in MEM supplemented with gentamycin, L-glutamine, nonessential amino acids and sodium selenite. For Vaco-5 cells, growth medium was supplemented with 8% calf serum. For RKO, SW480 and Vaco-457 cells, growth medium was supplemented with 2% fetal bovine serum (HyClone), 10 mg/liter bovine insulin, 2 mg/liter human transferin and 1 mg/liter hydrocortisone. Monolayer cultures were grown at 37° C. in a 5% $CO_2$ atmosphere. Genomic DNA was obtained by lysing cells in proteinase K buffer [10 mM Tris (pH 7.4)/10 mM EDTA/0.4% SDS/150 mM NaCl/100 µg/ml proteinase K] and extracting with phenol/chloroform/isoamyl alcohol (25:24:1).

Example 3

Serum as Bodily Fluid

Serum samples were prepared from whole blood immediately after collection of the blood. Serum samples were prepared by centrifuging the sample at 2700×g for 15 minutes and aspirating the serum. The serum was then stored at −80° C. until use. DNA was extracted from the serum by incubating 1 ml serum in a buffered extraction solution (140 mM Tris/ 140 mM EDTA/0.57% SDS) with proteinase K (500 µg) overnight at 50° C. in a shaking water bath. The sample was then subject to phenol:chloroform/chloroform DNA extraction twice, chloroform extraction, and ethanol precipitation. The precipitated DNA was resuspended in 25 µl distilled, deionized water and stored at −20° C. Approximately half of the sample was employed in the subsequent MSP assay.

Example 4

Bisulfite Treatment of DNA

DNA (1 µg) was treated with sodium bisulfite by dilution in 50 µl of distilled water and denaturation with 0.2 M sodium hydroxide for 15 minutes at 37° C. Thirty µl of 10 mM hydroquinone (Sigma) and 520 µl of 3 M sodium bisulfite (Sigma) at pH 5.0 were then added, and the samples were incubated at 53° C. for 18-20 hours. After treatment, the DNA was purified using the Wizard DNA Clean-Up System (Promega) following the manufacturer's protocol. The DNA was then desulphonated with 0.3 M sodium hydroxide for 10 minutes at room temperature, neutralized with 17 µl 10 M $NH_4OAc$, and then precipitated in 100% ethanol overnight at −80° C. The samples were resuspended in distilled water at a final concentration of approximately 50 ng/µl and stored at −80° C. for up to 8 weeks. A set of 4 known methylated and unmethylated control DNA samples were included in each round of bisulfite treatment.

Example 5

Methylation Specific PCR (MSP)

The compound-converted DNA was then subject to methylation specific PCR (MSP) using primer pairs as described in Example 1. The specific primers used were: methyl specific, SEQ. ID. NO. 2 and SEQ. ID. NO. 3; unmethyl specific, SEQ. ID. NO. 5 and SEQ. ID. NO. 6. The PCR was performed in 20-µl reaction volumes containing 1×PCR buffer II (Perkin-Elmer), 1.5 mM $MgCl_2$, 200 µM dNTP mixture (Perkin-Elmer), 1 µM of each primer, 100-150 ng modified DNA, and 1.5 units Amplitaq gold DNA polymerase (Perkin-Elmer). The thermocycler conditions were as follows: methyl-specific—95° C.×10', (92° C.×30", 62° C.×30", 70° C.×30")×39 cycles, final extension of 70° C.×7'; and unmethyl specific— 95° C.×10', (92° C.×30", 57° C.×30", 70° C.×30")×39 cycles, final extension of 70° C.×7'. The PCR products were subject to gel electrophoresis through a 2.5% agarose gel, stained with ethidium bromide, and then visualized with UV illumination using a digital imaging system (Alpha Inotech).

Example 6

Testing of Primers in MSP

The primers of Example 1 were tested for their specificity in amplifying compound-converted template sequences derived from methylated or unmethylated hMLH1 promoter DNA. The DNA of four cell lines (Example 2) that had been characterized as, respectively, demonstrating an unmethylated, active or a methylated inactive hMLH1 promoter was reacted with bisulfite (Example 4) and MSP was performed as in Example 5. DNA from cell lines V5 and RKO are known to have only methylated hMLH1 alleles (Deng, et al., 1999, Cancer Res, 59: 2029-33; Veigl, et al., 1998, Proc Natl Acad Sci USA, 95: 8698-702). DNA from cell lines SW480 and V457 are known to have only unmethylated hMLH1 alleles (Deng, et al., 1999, Cancer Res, 59: 2029-33; Veigl, et al., 1998, Proc Natl Acad Sci USA, 95: 8698-702).

Figure 1:
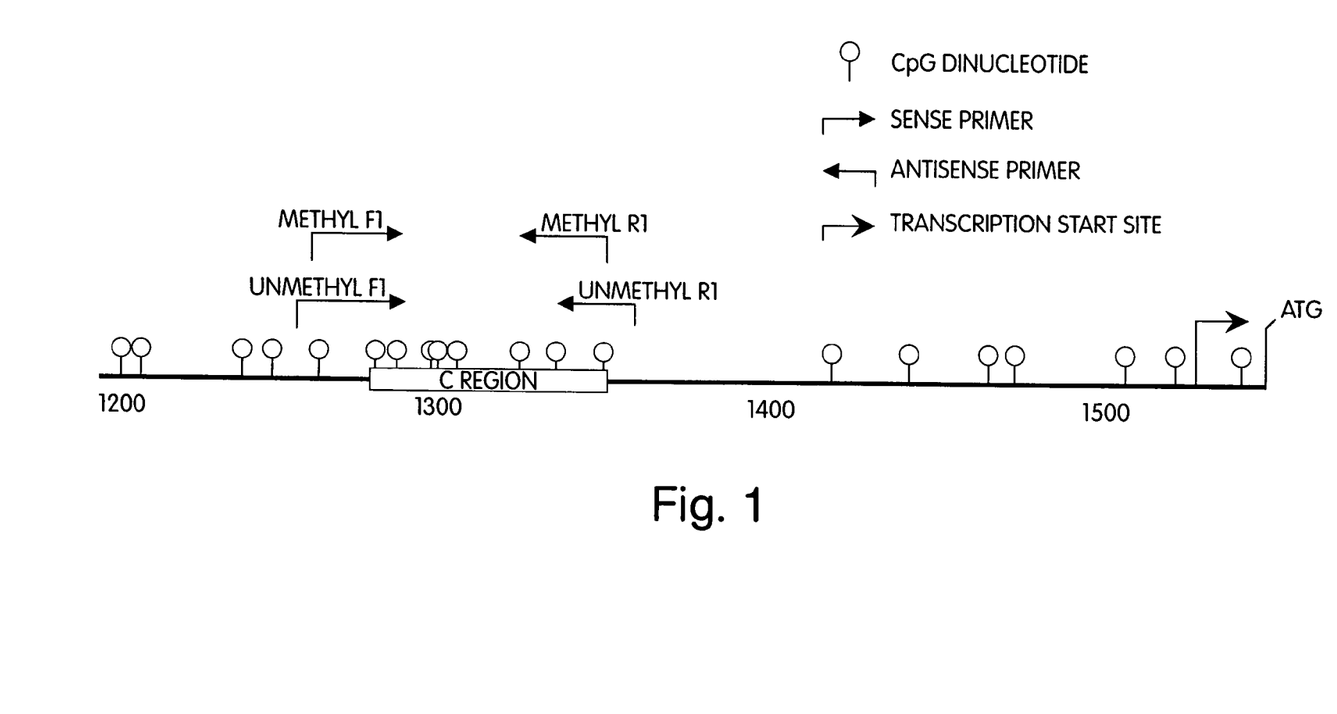
FIG. 1. Location of primers for hMLH1 methylation-sensitive polymerase chain reaction (MSP) assay in relation to the hMLH1 promoter C region identified by Deng et al. (Deng, et al., 1999, Cancer Res, 59: 2029-33). Primers cover 5 CpG dinucleotides in this region and are designed to specifically amplify chemically-converted sequences arising from either methylated ("methyl") or unmethylated ("unmethyl") templates. "F" indicates forward primer and "R" indicates reverse primer. The numbering scheme is based on the GenBank sequence entry U83845 (Kane, et al., 1997, Cancer Res, 57: 808-11).
Figure 4:
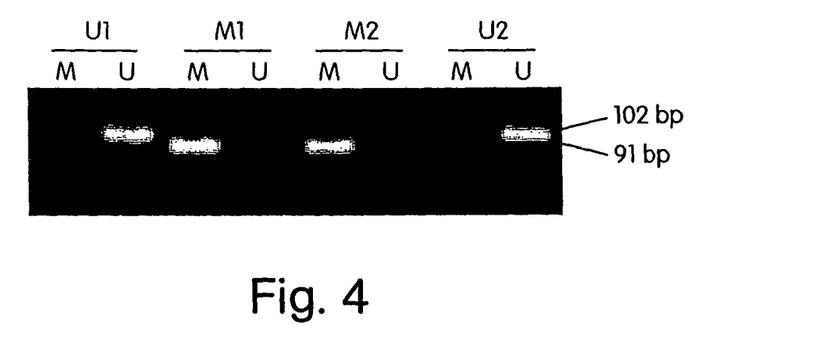
FIG. 4: Results of hMLH1 MSP assay using primers that amplify methylated (M) or unmethylated (U) alleles specifically. M1 and M2 are DNA samples from cell lines V5 and RKO, respectively, previously shown to have only methylated hMLH1 alleles; whereas, U1 and U2 are DNA samples from cell lines SW480 and V457, respectively, that have only unmethylated hMLH1 alleles (Deng, et al., 1999, Cancer Res, 59: 2029-33; Veigl, et al., 1998, Proc Natl Acad Sci USA, 95: 8698-702).

As shown in FIG. 4, a PCR product was obtained with the methylation-specific primer only from those cell lines known to have a methylated hMLH1 promoter.

Example 7

Sensitivity Test

To determine the sensitivity of the methylation specific PCR assay for detecting compound-converted template sequences from methylated hMLH1, DNA from cell lines with methylated hMLH1 alleles was mixed with DNA from cell lines bearing unmethylated hMLH1 alleles. These mixtures were treated with sodium bisulfite (Example 4) and then subjected to the MSP assay (Example 5).

The results of this study showed that a minimum of 1.0% of methylated DNA could be detected with this assay. Based on the amount of input DNA used in these reactions, the assay successfully detected the methylated hMLH1 promoter in 1.5 ng of total genomic DNA, which is equivalent to the amount of DNA present in 100-200 cells.

Example 8

MSP of DNA from Tumors

Primary colon cancer samples were obtained from nineteen patients. The MSI status of these colon cancers had been previously characterized. Of ten MSI colon cancers, ninety percent (n=9/10) demonstrated methylation of the hMLH1 promoter. In contrast, 0 of 9 microsatellite stable (MSS) colon cancer demonstrated hMLH1 promoter methylation. (See Table 2). Prior to the surgical resection of the tumors, matched serum samples were obtained from the patients.

Figure 5:
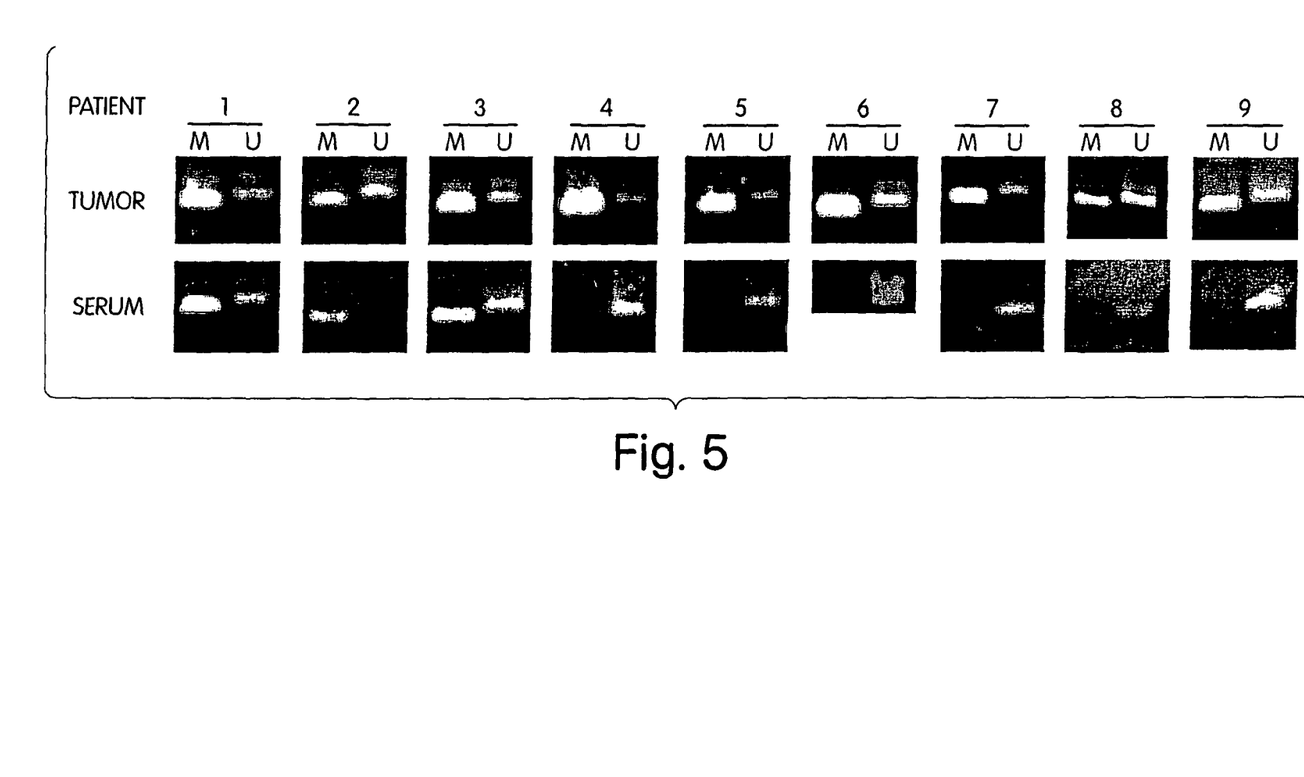
FIG. 5: Results of hMLH1 MSP from colon cancers and paired serum samples. (M) and (U), respectively, designate assays specific for amplification of the Methylated versus Unmethylated hMLH1 promoter. The unmethylated alleles detected in tumor samples likely represent contaminating normal tissue elements, and in serum samples likely arise from DNA released from circulating leukocytes.

Using the hMLH1 promoter MSP assay (Example 5), the DNAs extracted from the preoperative serum samples that matched these same 19 colon cancers were tested, after they had been treated with bisulfite (Example 4). Of nine individuals whose MSI colon cancers tested positive for hMLH1 promoter methylation, 33% (n=3/9) also demonstrated a positive assay for hMLH1 promoter methylation in DNA from their preoperative serum samples (See Table 2 and FIG. 5). A positive serum result was obtained in 2 of 2 individuals found at surgery to have distant metastases (stage D); in 1 of 3 individuals found to have nodal metastases (stage C), and in none of 4 individuals whose tumors proved to be confined to the colon (stage B). None of ten preoperative serum samples tested positive in the cases of individuals whose tumors lacked HMLH1 promoter methylation (Table 2). Individuals whose tumors lacked hMLH1 promoter methylation were similar to those whose tumors demonstrated hMLH1 promoter methylation with regards to stage, location of the primary tumors, and age of the patients at diagnosis. Thus, in this sample set, assay of serum DNA for hMLH1 promoter methylation demonstrated a sensitivity of 33% and a specificity of 100% for the detection of colon cancers bearing this molecular alteration.

TABLE 2

Results of hMLH1 MSP in tumors and serum of colon cancer patients Description of patient and tumor characteristics compared with results of hMLH1 MS-PCR analysis of matched tumor and serum samples.

| Patient no. | hMLH1 Tumor DNA/Serum DNA[a] | MSI status | Stage | Grade |
|---|---|---|---|---|
| 1 | M/M | MSI | D | Poor |
| 2 | M/M | MSI | D | Moderate |
| 3 | M/M | MSI | C | Poor |
| 4 | M/U | MSI | C | Moderate |
| 5 | M/U | MSI | C | Moderate |
| 6 | M/U | MSI | B2 | Moderate |
| 7 | M/U | MSI | B | Moderate |
| 8 | M/U | MSI | B | Moderate |
| 9 | M/U | MSI | A | Moderate |
| 10 | U/U | MSS | D | Moderate |
| 11 | U/U | MSS | D | Moderate |
| 12 | U/U | MSS | D | Poor |
| 13 | U/U | MSS | C | Moderate |
| 14 | U/U | MSS | B | Moderate |
| 15 | U/U | MSS | B | Moderate |
| 16 | U/U | MSS | B | Moderate |
| 17 | U/U | MSI | B | Moderate |
| 18 | U/U | MSS | B | Moderate |
| 19 | U/U | MSS | HGD[b] | HGD |

[a] M, methylated hMLH1 promoter; U, unmethylated hMLH1 promoter
[b] HGD, high-grade dysplasia in adenoma

What is claimed is:

1. A primer pair for detecting methylation of human mutL homolog 1 (hMLH 1) promoter DNA, wherein the primer pair comprises a primer consisting of the nucleotide sequence of SEQ ID NO: 2 and a primer consisting of the nucleotide sequence of SEQ ID NO: 3.

2. The primer pair of claim 1, wherein at least one primer is labeled with a detectable marker.

3. The primer pair of claim 1, wherein said at least one primer is labeled with a fluorescent dye.

* * * * *

SEQUENCE LISTING

<160> NUMBER OF SEQ ID NOS: 11

<210> SEQ ID NO 1
<211> LENGTH: 1554
<212> TYPE: DNA
<213> ORGANISM: Human

<400> SEQUENCE: 1

```
acgcttccat ttcttttctt agagagaata ttagttttaa agtttccct  ctcctaagcc      60 aattgttcag acatcgtcca ttaacccttt caccatgctc tgattcagat tccgttagta    120
aagtctgaaa ttcaggtcgc ctaacgcctc tggtcttaat caaaactatc cattcggata    180
tggtatttat gatctgatta acatctacat cataggagct caacagttcc aagtgaagaa    240
atcctgaata atgaatgaca ttccaacagt tggggcttac ggccttttct ctcatgtatg    300
```

```
agacgagtcc tgagttctca ccaatcatcc tcaaagtatg ggtcgtggtc agtccaacca      360
ttctctgcaa gctaagccct gctgtctgca gggactctag gattgccgac atgagcgcac      420
caacactgaa atgatgagtc aggttgatta tggtcagaag atcttcttgc acctccaact      480
cagggcctac accgcggata agaccagga ggtagttctc ataggccaca aaagcctggt       540
cgtccaaggc aagagaatag gctttaaagt ccctggctcg gttaaaaagc tggttgcgta      600
gattcctgtc aatgctcagg atcctctgcc ttgtgatatc tggagataag tcaacgcctt      660
gcaggacgct tacatgctcg ggcagtacct ctctcagcaa cacctccatg cactggtata      720
caaagtcccc ctcaccccag ccgcgaccct tcaaggccaa gaggcggcag agcccgaggc      780
ctgcacgagc agctctctct tcaggagtga aggaggccac gggcaagtcg ccctgacgca      840
gacgctccac cagggccgcg cgctcgccgt ccgccacata ccgctcgtag tattcgtgct      900
cagcctcgta gtggcgcctg acgtcgcgtt cgcgggtagc tacgatgagg cggcgacaga      960
ccaggcacag ggccccatcg ccctccggag gctccaccac caaataacgc tgggtccact     1020
cgggccggaa aactagagcc tcgtcgactt ccatcttgct tcttttgggc gtcatccaca     1080
ttctgcggga ggccacaaga gcagggccaa cgttagaaag gccgcaaggg gagaggagga     1140
gcctgagaag cgccaagcac ctcctccgct ctgcgccaga tcacctcagc agaggcacac     1200
aagcccggtt ccggcatctc tgctcctatt ggctggatat ttcgtattcc ccgagctcct     1260
aaaaacgaac caataggaag agcggacagc gatctctaac gcgcaagcgc atatccttct     1320
aggtagcggg cagtagccgc ttcagggagg gacgaagaga cccagcaacc cacagagttg     1380
agaaatttga ctggcattca agctgtccaa tcaatagctg ccgctgaagg gtggggctgg     1440
atggcgtaag ctacagctga aggaagaacg tgagcacgag gcactgaggt gattggctga     1500
aggcacttcc gttgagcatc tagacgtttc cttggctctt ctggcgccaa aatg          1554

<210> SEQ ID NO 2
<211> LENGTH: 28
<212> TYPE: DNA
<213> ORGANISM: Artificial Sequence
<220> FEATURE:
<223> OTHER INFORMATION: PCR primer for detection of methylated hMLH1
      DNA

<400> SEQUENCE: 2
aacgaattaa taggaagagc ggatagcg                                          28

<210> SEQ ID NO 3
<211> LENGTH: 27
<212> TYPE: DNA
<213> ORGANISM: Artificial Sequence
<220> FEATURE:
<223> OTHER INFORMATION: PCR primer for detection of methylated hMLH1
      DNA

<400> SEQUENCE: 3
cgtccctccc taaaacgact actaccc                                           27

<210> SEQ ID NO 4
<211> LENGTH: 31
<212> TYPE: DNA
<213> ORGANISM: Artificial Sequence
<220> FEATURE:
<223> OTHER INFORMATION: PCR primer for detection of methylated hMLH1
      DNA

<400> SEQUENCE: 4
```

```
aaaaatgaat taataggaag agtggatagt g                                    31

<210> SEQ ID NO 5
<211> LENGTH: 32
<212> TYPE: DNA
<213> ORGANISM: Artificial Sequence
<220> FEATURE:
<223> OTHER INFORMATION: PCR primer for detection of methylated hMLH1
      DNA

<400> SEQUENCE: 5
taaaaatgaa ttaataggaa gagtggatag tg                                   32

<210> SEQ ID NO 6
<211> LENGTH: 25
<212> TYPE: DNA
<213> ORGANISM: Artificial Sequence
<220> FEATURE:
<223> OTHER INFORMATION: PCR primer for detection of methylated hMLH1
      DNA

<400> SEQUENCE: 6
aatctcttca tccctcccta aaaca                                           25

<210> SEQ ID NO 7
<211> LENGTH: 29
<212> TYPE: DNA
<213> ORGANISM: Artificial Sequence
<220> FEATURE:
<223> OTHER INFORMATION: PCR primer for detection of methylated hMLH1
      DNA

<400> SEQUENCE: 7 cgttttttttt tgaagcggtt attgtttgt                                      29

<210> SEQ ID NO 8
<211> LENGTH: 28
<212> TYPE: DNA
<213> ORGANISM: Artificial Sequence
<220> FEATURE:
<223> OTHER INFORMATION: PCR primer for detection of methylated hMLH1
      DNA

<400> SEQUENCE: 8
aacgaaccaa taaaaaaac aaacaacg                                         28

<210> SEQ ID NO 9
<211> LENGTH: 32
<212> TYPE: DNA
<213> ORGANISM: Artificial Sequence
<220> FEATURE:
<223> OTHER INFORMATION: PCR primer for detection of methylated hMLH1
      DNA

<400> SEQUENCE: 9
taaaaacgaa ccaataggaa gagcggacag cg                                   32

<210> SEQ ID NO 10
<211> LENGTH: 32
<212> TYPE: DNA
<213> ORGANISM: Artificial Sequence
<220> FEATURE:
<223> OTHER INFORMATION: PCR primer for detection of methylated hMLH1
      DNA

<400> SEQUENCE: 10
taaaaacgaa uuaataggaa gaguggauag cg                                   32
```

```
<210> SEQ ID NO 11
<211> LENGTH: 32
<212> TYPE: DNA
<213> ORGANISM: Artificial Sequence
<220> FEATURE:
<223> OTHER INFORMATION: PCR primer for detection of methylated hMLH1
      DNA

<400> SEQUENCE: 11
taaaaaugaa uuaataggaa gaguggauag ug                                      32
```